US007604997B2

(12) United States Patent
Esswein et al.

(10) Patent No.: US 7,604,997 B2
(45) Date of Patent: Oct. 20, 2009

(54) WIPES AND METHODS FOR REMOVAL OF METAL CONTAMINATION FROM SURFACES

(75) Inventors: Eric J. Esswein, Conifer, CO (US); Mark F. Boeniger, Cincinnati, OH (US); Kevin E. Ashley, Cincinnati, OH (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 826 days.

(21) Appl. No.: 11/039,178

(22) Filed: Jan. 18, 2005

(65) Prior Publication Data

US 2006/0160230 A1 Jul. 20, 2006

(51) Int. Cl.
*G01N 33/20* (2006.01)
*G01N 21/25* (2006.01)

(52) U.S. Cl. .......................... 436/82; 162/127; 422/56; 422/57; 422/61; 436/73; 436/81; 436/166; 436/169; 436/171; 510/130; 510/138

(58) Field of Classification Search .................. 162/76, 162/111, 127; 210/773; 422/56–58, 61; 424/414, 443; 436/73, 77, 81–82, 166, 169, 436/171; 510/130, 138, 155
See application file for complete search history.

(56) References Cited

U.S. PATENT DOCUMENTS

| | | | | | |
|---|---|---|---|---|---|
| 4,096,311 | A | * | 6/1978 | Pietreniak | 442/59 |
| 4,168,302 | A | * | 9/1979 | Schoenberg | 424/70.19 |
| 4,828,912 | A | * | 5/1989 | Hossain et al. | 442/123 |
| 5,010,020 | A | * | 4/1991 | Gould | 436/77 |
| 5,019,516 | A | * | 5/1991 | Wiese | 436/77 |
| 5,364,792 | A | * | 11/1994 | Stone | 436/73 |
| 5,492,835 | A | * | 2/1996 | Koenig | 436/77 |
| 5,558,835 | A | * | 9/1996 | Kozarsky et al. | 422/56 |
| 5,681,802 | A | * | 10/1997 | Fujiwara et al. | 510/130 |
| 5,702,992 | A | * | 12/1997 | Martin et al. | 442/123 |
| 5,904,810 | A | * | 5/1999 | Schroeder et al. | 162/111 |
| 5,916,586 | A | * | 6/1999 | Villa et al. | 424/443 |
| 5,935,880 | A | * | 8/1999 | Wang et al. | 442/65 |
| 6,017,861 | A | * | 1/2000 | Fujiwara et al. | 510/130 |
| 6,129,815 | A | * | 10/2000 | Larson et al. | 162/112 |
| 6,248,593 | B1 | | 6/2001 | Esswein et al. | |
| 6,315,864 | B2 | * | 11/2001 | Anderson et al. | 162/109 |
| 6,323,036 | B1 | * | 11/2001 | Chapoteau et al. | 436/74 |
| 6,416,623 | B1 | * | 7/2002 | Hollmark et al. | 162/109 |
| 6,737,068 | B2 | * | 5/2004 | Durden | 424/401 |
| 7,482,021 | B1 | * | 1/2009 | Tison et al. | 424/402 |
| 2002/0155281 | A1 | * | 10/2002 | Lang et al. | 428/337 |
| 2003/0143263 | A1 | * | 7/2003 | Durden et al. | 424/443 |
| 2004/0161991 | A1 | * | 8/2004 | Walton et al. | 442/327 |
| 2005/0045293 | A1 | * | 3/2005 | Hermans et al. | 162/109 |

OTHER PUBLICATIONS

Askin et al., “Effect of Personal Hygiene on Blood Lead Levels of Workers at a Lead Processing Facility,” *American Industrial Hygiene Association Journal*, 58:752-753, 1997.

Burr et al., Niosh Health Hazard Evaluation Report No. 99-0188, “YUASA, Inc., Sumter, South Carolina,” Washington D.C.:Government Printing Office, 2000.

Chavez et al., “Surfactant Enhanced In-Situ Soil Washing for the Removal of Heavy Metals from Contaminated Soil,” Paper No. 002001, Presented at the 2000 ASAE International Meeting, Milwaukee, Wisconsin, 2000 (abstract only).

Eisenberg et al., “Lead Dust Transport from Firing Ranges on the Footwear of Recreational Shooters—A Pilot Study,” presented at National Institute for Occupational Safety and Health, Cincinnati, Ohio, 2003 (abstract only).

Kornicki et al., “Cationic Surfactant Feasibility for Use in Removal of Lead from Soil,” *Environmental Geosciences*, 5(1):29-38, 1998.

Kornecki et al., “Saturated Column Feasibility Study Using Cationic Surfactants for In Situ Removal of Lead from Soil,” *Environmental Geosciences*, 6(1):42-52, 1999.

“D-Lead Abrasive Hand Soap,” UniqueTek Inc., http://www.uniquetek.com/site/696296/product/T1232, 2003.

“Full Disclosure,” Publication 1630, SKC Inc., 2002.

Reh, “*Health Hazard Evaluations: Issues Related to Occupational Exposure to Lead, 1994 to 1999*,” DHHS (NIOSH) Publication No. 2001-113, ed. by Weber, Washington D.C.:Government Printing Office, 2001.

Mackalene™ 426 Product Information, McIntyre Group Ltd., 2002.

Esswein et al., Niosh Health Hazard Evaluation Report No. 91-0366-2453, “Delaware County Resource Recovery Facility, Chester, Pennsylvania,” Washington D.C.:Government Printing Office, 1994.

Esswein et al., Niosh Health Hazard Evaluation Report No. 94-0268-2618, “Standard Industries, San Antonio, Texas,” Cincinnati:NIOSH Publications Office, 1996.

Ashley et al., “Protecting Workers Exposed to Lead-Based Paint Hazards: A Report to Congress,” ed. by Sussell, Cincinnati, NIOSH Publications Office, 1997.

“A Question and Answer Overview: Micrex/Wet Wipe Process™,” Micrex Corporation, 2002.

“Standard Test Method for Determining the Dynamic Wiping Efficiency of Nonwoven Fabrics Not Used in Cleanrooms,” D 6702-01, ASTM International, 2001.

* cited by examiner

*Primary Examiner*—Arlen Soderquist
(74) *Attorney, Agent, or Firm*—Klarquist Sparkman LLP

(57) ABSTRACT

Wipes, methods and kits useful for testing and/or removal of metal from surfaces (such as, dermal surfaces) are disclosed. Exemplar wipes, including the combination of a three-dimensionally textured absorbent support, a cationic surfactant, and a weak acid, are disclosed. In some examples, the cationic surfactant is isostearamidopropyl morpholine lactate (ISML), and the weak acid is citric acid.

27 Claims, 4 Drawing Sheets

WIPES AND METHODS FOR REMOVAL OF METAL CONTAMINATION FROM SURFACES

FIELD

This disclosure generally relates to wipes, methods and kits for removing metal contamination, such as, lead contamination, from surfaces, including, for example, dermal surfaces of humans or other animals.

BACKGROUND

Increasing occupational and environmental exposure to metals and metal-based compounds, which are inherently toxic to biological systems, raises concerns about their potential effects on the health and well being of living organisms. Exposure to such metals is a significant problem that affects a large and diverse segment of the population. Five of the top 20 hazardous substances (including the top three hazardous substances) on the Comprehensive Environmental Response, Compensation, and Liability Act (CERCLA) Priority List of Hazardous Substances for 2003 are metals, including arsenic, lead, mercury, cadmium, and chromium (hexavalent). In 2003, exposures to lead were the number 1 environmental health hazard for children.

Exposure to metals may occur in a wide variety of locations, including in the workplace, in homes or schools, or in the outdoor environment. Skin contact is one significant route of exposure to metals or metal compounds, at least, because (i) metals may be absorbed through the skin; (ii) skin can act as a reservoir for metals; (iii) skin surface deposition can be an important source of secondary contamination; and (iv) impairment or loss of skin barrier function can occur. Unfortunately, many metals typically are not simply washed off of the skin. Surveys of industrial wash rooms show most potentially contaminated workers invest less than 60 seconds cleaning up before breaks. However, most conventional industrial soaps require 5 to 10 minutes of continuous washing to reduce surface concentrations of powdered metals (such as, lead) to levels that are not likely to present potential health hazards. Thus, significant metal contamination may remain after washing (Esswein and Tepper, NIOSH Health Hazard Evaluation Report No. 91-0366-2453, Delaware County Resource Recovery Facility, Chester, Pa., CDC/NIOSH:Cincinnati, Ohio, 1991; Esswein et al., NIOSH Health Hazard Evaluation Report No. 94-0268-2618, Standard Industries, San Antonio, Tex., CDC/NIOSH:Cincinnati, Ohio, 1996, Mattorano, NIOSH Health Hazard Evaluation Report No. 94-0273-2556, Bruce Mansfield Power Station, Shipping port, PA, CDC/NIOSH:Cincinnati, Ohio, 1996).

Lead provides a particularly useful example of the challenges posed by metal exposure. Lead exposure can occur, for example, to workers involved (and others in the area) in removal of lead-based paints and/or the renovation of structures containing lead-based paints, workers in metal working and other metal related industries, workers in other industrial facilities, as well as adults or children living within or visiting homes or schools containing lead-based paints. Prolonged and repeated exposure to workers involved in removal or abatement of lead-based paints and exposure of children in homes and schools is especially damaging. Lead residues on human skin, especially on the hands, of industrial workers (as well as others) can be a significant health risk since such residues may be ingested during normal activities (e.g., eating, drinking, and smoking).

Methods for detecting the presence of lead are available. While such detection methods may be useful to disclose the presence or absence of lead, detection methods are not designed to remove lead from the surface tested. Compositions and methods are needed to remove metals, such as lead.

To that end, efforts have been directed to removing lead from liquids, including drinking water (see, e.g., U.S. Pat. Nos. 5,665,240; and 6,106,725), liquid hydrocarbons (see, for example, U.S. Pat. Nos. 4,424,120; 4,424,119; and 5,952,541), machining coolant solutions (see, e.g., U.S. Pat. No. 5,520,815), phosphoric acid (see, e.g., U.S. Pat. No. 5,431,895), and other aqueous solutions (see, e.g., U.S. Pat. Nos. 4,010,186; 4,956,154; 4,994,191; 5,053,139; and 5,286,464). Lead desorption from contaminated soil has also been described (see, e.g., Komecki et al., *Environ. Geosci.*, 6(1): 42-52, 1999). The physical properties of liquids and soil permit physical mixing of contaminated liquids or soils with decontaminating agents on a microscopic level that cannot be achieved with non-dispersible (such as, solid) matter. As a result, it may be more difficult to contact and remove metal contamination from a solid surface, especially where the surface has interstices where contaminants can lodge (such as, skin). Moreover, agents suitable for lead decontamination of liquid or soil may cause damage to solid surfaces and, in particular, may irritate or harm sensitive surfaces such as human skin.

Comparatively few methods of removing lead or other potentially harmful metals from a solid surface are described. Lead-containing paint provides one application; however, the described methods involve harsh physical methods (e.g., hot air blowers combined with scraping) and/or caustic chemicals (such as, methylene chloride, toluene, acetone, calcium hydroxide, magnesium hydroxide, and sodium hydroxide; see, e.g., U.S. Pat. No. 5,964,961). These methods are unsuitable for applications where no substantial modification or damage to the surface is desired; such as, for example, removal of lead (or other metals) from human skin.

Products that claim to remove lead from human skin contain active ingredients such as EDTA (see, Askin and Volkmann, *Am. Ind. Hyg. Assoc. J.*, 58:752-753, 1997) or anionic surfactants (see, D-Wipe®; Esca Tech, Inc.; Milwaukee, Wis.). EDTA is a suspected persistent environmental pollutant and a skin irritant, which may cause reddening or inflammation on prolonged skin contact. Anionic surfactants may also cause skin irritation, such as dryness and scaling, and may further lead to high levels of foaming. Moreover, anionic surfactants may not be fully effective in removing lead contamination.

It is desirable, therefore, to provide safe, reliable and effective compositions and methods for removing metals, such as lead, from surfaces, including human skin. Of particular need are compositions and methods that do not substantially damage the treated surface, or unduly irritate biological surfaces, such as skin.

SUMMARY

Disclosed herein are wipes (such as handwipes) that include a three-dimensionally textured absorbent support (such as a support with a microcrepe surface), and isostearamidopropyl morpholine lactate (ISML) and citric acid in the absorbent support. In particular embodiments, the amount of ISML in the absorbent support is from about 0.3 gm to about 2 gm ISML per gram of absorbent support (such as, from about 0.6 gm to about 1.3 gm ISML per gram of absorbent support). In other embodiments, the amount of citric acid in the absorbent support is 0.01 gm to about 0.1 gm citric acid per gram of absorbent support (for example, from about 0.03 gm to about 0.07 gm citric acid per gram of absorbent support). In more particular examples, the weight ratio of the amount of ISML to the amount of citric acid in the absorbent support is 12.5 parts ISML to about 0.5 parts citric acid.

More particular wipe embodiments include a three-dimensionally textured (for instance, microcreped) absorbent support, ISML, and a weak acid (such as citric acid, or acetic acid, or a combination thereof), and the amounts of ISML and the weak acid(s) in the wipe are sufficient to solubilize a metal (such as, lead, cadmium, tin, barium, arsenic, chromium, copper, lead, mercury, silver, zinc, strontium, thallium, germanium, or zirconium, or a combination thereof).

Also disclosed herein are methods for removing metals from a surface (for instance a dermal surface). Such methods involve (i) applying a cationic surfactant and a weak acid to a surface, and (ii) wiping the surface with a three-dimensionally textured absorbent support; wherein wiping the surface removes at least one metal (such as, lead, cadmium, tin, barium, arsenic, chromium, copper, lead, mercury, silver, zinc, strontium, thallium, germanium, or zirconium, or a combination thereof) from the surface. In certain method embodiments, the cationic surfactant is ISML, lapryium chloride, cetyltrimethylammonium bromide, di-dodecyldimethylammonium bromide, trimethylbenzylammonium chloride, diethyl ester dimethyl ammonium chloride, hexadecyltrimethylammonium, tetradecyl trimethyl ammonium bromide, cetylpyridinium chloride, alkyl $C_{12}$-$C_{14}$-dimethylbenzyl ammonium chloride, dodecyl pyridinium chloride, 11-(acryloyloxy)undecyl(trimethyl)ammonium bromide, dimethyl dioctadecyl ammonium bromide, or N-alkyl dimethylbenzyl ammonium chloride, or a combination thereof. In more particular method embodiments, the cationic surfactant is ISML and, in some such embodiments, the concentration of ISML on the surface is from about 25 $\mu g/cm^2$ to about 250 $\mu g/cm^2$. In other method embodiments, the weak acid is citric acid, acetic acid, ascorbic acid, glycolic acid, maleic acid, fumaric acid, benzoic acid, salicylic acid, nicotinic acid, cinnamic acid, tartaric acid, or mandelic acid, or a combination thereof. Particular methods involve citric acid and, in some cases, the concentration of citric acid on the surface is from about 1 $\mu g/cm^2$ to about 10 $\mu g/cm^2$. Particular exemplar methods involve an absorbent support containing the cationic surfactant and the weak acid.

Other disclosed methods are, more particularly, for removing lead from a dermal surface. Such methods involve (i) providing an absorbent support, which includes a three-dimensionally textured surface, at least about 50% (w/w) of a cationic surfactant, and at least about 0.5% (w/w) of a weak acid; and (ii) wiping a dermal surface with the absorbent support to remove lead from the dermal surface. In some methods, the three-dimensionally textured surface is a microcrepe surface, the cationic surfactant is ISML, and the weak acid is citric acid, acetic acid or a combination thereof. In some instances, a method also involves testing for the presence of lead on the dermal surface prior to or following steps (i) and (ii). In other exemplar methods, steps (i) and (ii) are repeated if a testing step indicates the continued presence of lead on the dermal surface.

Kits for removing lead from a surface (such as, a dermal surface) are also disclosed. Such kits comprise any of the disclosed wipes and instructions for removing lead from the surface using the wipe(s). In particular embodiments, a kit for detecting and removing lead from a surface includes (i) a means for detecting lead on a surface, (ii) at least one wipe disclosed herein, and (iii) instructions for detecting lead on the surface and for removing lead from the surface with the wipe(s). In some kit embodiments, a means for detecting lead includes a hand wipe, an acidic aqueous solution having a pH of about 1 to about 5, and a lead-detecting calorimetric reagent (such as, rhodizonate anion or sulfide anion).

DETAILED DESCRIPTION

I. Abbreviations and Terms

ISML isostearamidopropyl morpholine lactate

PEL permissible exposure limit

Figure 1:
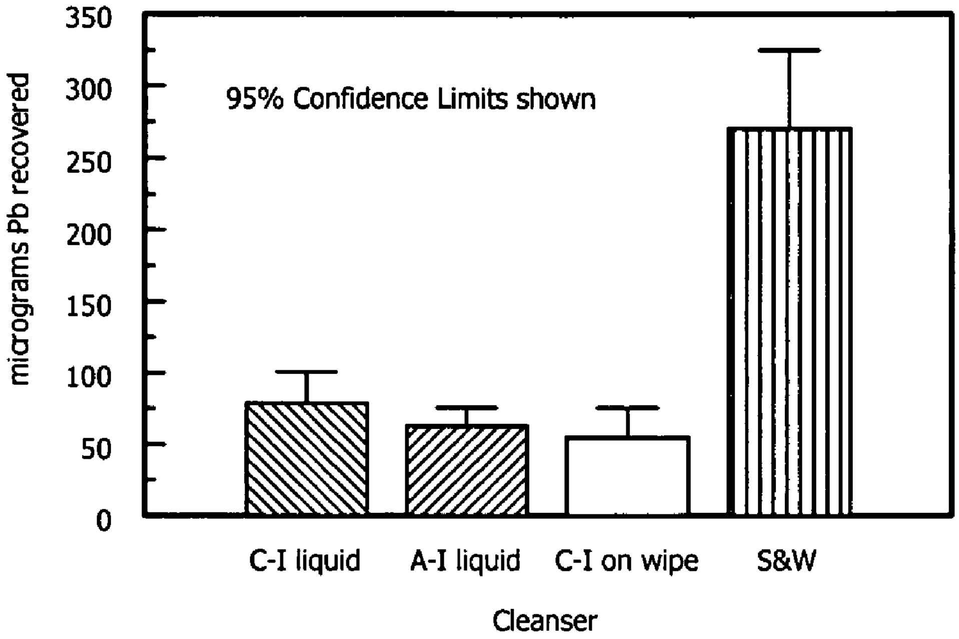
FIG. 1 is a bar graph showing the amount of a 3000 μg initial lead load remaining on human hands after cleansing protocols employing a liquid mixture of acetic acid and ISML ("A-I"), a liquid mixture of citric acid and ISML ("C-I"), a BabyWipe™ to which a liquid mixture of citric acid and ISML had been applied ("C-I on wipe"), and a common soap with water ("S&W").

Unless otherwise noted, technical terms are used according to conventional usage. In order to facilitate review of the various embodiments of the invention, the following explanations of specific terms are provided:

Absorbent support: A typically woven or nonwoven, fibrous matrix or material, such as, fabric, paper, or cellulose, carbohydrates (such as, sugars), starches, plastic or mixtures thereof, which is used to physically touch and rub a surface usually without resulting in significant deterioration or degradation of the material. An absorbent support is capable of incorporating other materials, including fluids (such as, a cationic surfactant or a weak acid), on or within the support. Such interactions may include absorption or adsorption onto the surface and/or into a matrix of fibers comprising the absorbent support. Though permissible in each case, the term "absorbent" does not require (i) saturation of the support with the added substance, or (ii) that the added substance is homogeneously distributed upon or within the support.

Cationic surfactant: A surfactant molecule that can dissociate to yield a surfactant ion whose polar group is positively charged. A "surfactant" (also called a "surface acting agent) is a substance that lowers the surface or interfacial tension of the medium in which the surfactant is dissolved. Surfactant molecules have a hydrophilic portion, which associates with water, and a hydrophobic portion, which avoids water. In the absence of other hydrophobic molecules, the hydrophobic portion of the surfactant molecule protrudes from the surface of a water drop. As a result, the water molecules in the drop are disrupted and can no longer form a strong surface tension, so the water drop no longer beads up, but spreads. The hydrophobic end of a surfactant molecule, which protrudes from the water drop, is also free to attach to hydrophobic molecules or particles (such as, grease, fat, or oil) on the surface.

Cationic surfactants include, for example, quaternary ammonium derivatives (e.g., aliphatic, aromatic and heterocyclic quaternaries and their respective salts such as benzalkonium chloride or alkylaryl quaternary salt); amidoamines (e.g., amidoamine salts and oxides); and betaines (e.g., N-alkylbetaines). In one particular example, the cationic surfactant is isostearamidopropyl morpholine lactate (ISML), which can dissociate to yield a positively charged isostearamidopropyl morpholine group and a functional lactic acid ion group.

Contaminant: A substance, such as a potentially harmful metal (for example, lead), that is either present in an environment (such as, on a surface) where it does not belong or is present at levels that present exposure risks that might cause adverse health effects in a subject, such as a human.

Exposure: The state of being exposed to a chemical, physical or biological agent, such as a potentially harmful metal. Exposure to the agent may occur by a variety of methods including, without limitation, dermal contact, inhalation, or ingestion.

Lead: Elemental lead in any ionic or nonionic state or lead in any compound form (such as lead oxides or lead halides). Particular examples include $Pb^0$, $Pb^{2+}$, $PbO_2$, $Pb_3O_4$, $PbCl_2$ or $PbCO_3$.

Metal or potentially harmful metal: A metal, metal ion, or metal-containing compound (or other chemical form of a metal) with the potential to adversely effect the health or well being of living organisms (such as humans), which are exposed to the metal. The harmful effect of the metal on the living organism may be observed relatively soon after exposure to the metal, or may occur over an extended period of time. The adverse effects of a potentially harmful metal may result after a single exposure or after multiple exposures. Potentially harmful metals often, but not always, have a relatively high atomic mass; for example, lead is a relatively high mass metal that has a known potential to harm living organisms, while beryllium is an example of a relatively low mass potentially harmful metal.

Representative potentially harmful metals, include, lead, cadmium, tin, barium, beryllium, arsenic, chromium, copper, lead, mercury, silver, zinc, strontium, thallium, cobalt, germanium, or zirconium. In particular examples, a metal cation having a +2 charge (such as, $Pb^{2+}$, $Ba^{2+}$, $Be^{2+}$, $Co^{2+}$, $Ni^{2+}$, $Pd^{2+}$ $Pt^{2+}Hg^{2+}Zn^{2+}$, $Cd^{2+}$, or $Sn^{2+}$) is a potentially harmful metal. In other examples, metal oxides, such as $AsO_3$, MnO, $MnO_2$, $PbO_2$, $Pb_3O_4$, or particular lead-containing compounds, such as $PbCl_2$ or $PbCO_3$, are potentially harmful metals.

Remove [a metal from a surface]: Displace an amount or concentration of metal from a surface (such as, a dermal surface) by physical or chemical methods or a combination thereof (as further described and/or exemplified elsewhere in this specification).

Solubilize: To dissolve; for example, to disperse on the molecular level into a solvent.

Surface: The non-dispersible outer layer of an organism or a tangible, solid object. Representative surfaces include, for example, dermal surfaces (such as hands), floors, walls, windowsills, clothing, laundry, shoes, equipment surfaces, and furniture surfaces. A "dermal surface" refers to the skin (such as the strateum corneum) of an animal, including, for example, mammals (such as humans). More generally, "integument" refers to the outer protective surface covering an animal or a plant.

Three-dimensionally textured [absorbent support]: An absorbent support having at least one surface that is not planar. A three-dimensionally textured absorbent support will have a comparatively rough surface with protrusions (such as, a succession of ridges and grooves) above (or above and below) the surface of the absorbent support. Such protrusions may be visible only on the microscopic level or may be visible to the naked eye. Three-dimensional texturing increases the surface area of an absorbent support in comparison to a surface lacking such protrusions or texturing effects. Three-dimensional texturing also is believed to increase frictional resistance of an absorbent support as it is moved across a surface. Although bound by theory, such increased frictional resistance may enhance mechanical removal of contaminants present on a surface. Examples of three-dimensionally textured surfaces are found in U.S. Pat. App. No. 2002/0193029 and PCT Pub. No. WO 02/076723 and elsewhere in this specification. One particular example of a three-dimensionally textured surface is called a "microcrepe surface," which is described, for example, in PCT Pub. No. WO 02/076723, and which is discussed in more detail below.

Weak acid: An acid that, upon transient exposure, does not (i) cause undue skin irritation in a living organism, or (ii) substantially damage to the surface of a tangible object. Specific examples of weak acids are provided elsewhere in this specification. Transient exposure to a weak acid may be as brief as about one minute, about two minutes or up to about five minutes; however, depending on the nature of the particular weak acid, exposures of up to about 60 minutes, or even up to about 24 hours or longer may be sufficiently transient to avoid undue skin irritation or substantial damage to another surface by the weak acid. Undue skin irritation may include, for example, cracking of the skin surface, bleeding, ulcers, or prolonged redness, itching, soreness, or dryness of the skin. Substantial damage to the surface of a tangible object may include, for example, etching or pitting of the surface, or removal of or damage to any finish in or on the surface (such as, paint, varnish, shellac, or dye).

Unless otherwise explained, all technical and scientific terms used herein have the same meaning as commonly understood by one of ordinary skill in the art to which the disclosed subject matter belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A or B, or including A and B. It is further to be understood that any quantitative values are approximate whether the word "about" or "approximately" or the like are stated or not. All publications, patent applications, patents, and other references mentioned herein are incorporated by reference in their entirety. In addition, the materials, methods, and examples described herein are illustrative only and not intended to be limiting.

II. Wipes and Other Compositions for Removing Metals

Provided herein are wipes, which are useful for, among other things, methods of removing metals from surfaces (particular method embodiments are discussed below in more detail). The disclosed wipes generally comprise an absorbent support, a cationic surfactant, and a weak acid. Although not bound by theory, it is believed that the wipes work additively or synergistically involving mechanical (such as, physical dislodgement) and chemical mechanisms to remove metal contamination, for instance, from skin or other surfaces. In some examples, chemical mechanisms of removal can include solubilization, ionization, alteration of pH and/or chelation of a metal contaminant.

1. Absorbent Support

An absorbent support of any suitable shape may be used to practice the disclosed methods and to form the disclosed apparatus. For example, the support may be round, square, rectangular, triangular, polygonal, or irregularly shaped. In particular embodiments, the support may be a sheet of absorbent material, an absorbent cloth, a sponge, a swab, pad, or engineered cloth.

The absorbent support can be any size that is useful for any particular metal removal application. For example, the absorbent support may be proportional in size to the surface from which metal is to be removed. In the case of dermal surfaces, for example, a useful absorbent support may be the size of a hand wipe, towelette or wet wipe, each of which are commonly known in the art (see, for example, hand wipes, towelettes or wet wipe commercially available from or manufactured by DuPont (Wilmington, Del.), First Quality Nonwovens (Great Neck, N.Y.), Kimberley Clark (Roswell, Ga.), Yo Yi Enterprise Co., Ltd. (Taiwan), Chan Guare Industy Co., Ltd. (Taiwan), Chicopee (Dayton, N.J.), Polymer Group, Inc. (Mooresville, N.C.), Georgia Pacific (Atlanta, Ga.), Nice Pak (Orangeburg, N.Y.), The Dial Corporation (Scottsdale, Ariz.), Scott Paper Company (Philadelphia, Pa.), Procter & Gamble Co. (Cincinnati, Ohio), The Wilkins Company, Inc. (Cortland, N.Y.), AGI Industries, Inc. (Lake Forest, Calif.) and others. Alternatively, the absorbent support may be sized to accommodate particular packaging. Such size determinations are well within the ordinary skill in the art. In particular examples, an absorbent support can be about 8" ×about 8" (about 20 cm×about 20 cm) or about 4" ×about 4" (about 10 cm×about 10 cm). In even more particular examples, a pediatric-sized wipe (e.g., for lead removal from the skin of children) can be about 4" ×about 4" (about 10 cm×about 10 cm).

The absorbent support can be made of any material known in the art that is capable of absorbing or holding other material(s), particularly cationic surfactants and or weak acids, while retaining sufficient structural integrity to be wiped across a surface with sufficient force and/or repetition to remove metal surface contaminants. Representative absorbent materials include woven or nonwoven matrices of natural fibers, synthetic fibers, or mixtures of natural and synthetic fibers. Suitable natural fibers include but are not limited to cellulosic fibers, such as wood pulp fibers and cotton. Suitable synthetic fibers include fibers commonly used in textiles, including but not limited to rayon, and polyolefins, such as polyester and polypropylene fibers.

Any of several materials known by those of ordinary skill in the art are contemplated for use as an absorbent support herein (see, for example, U.S. Pat. No. 4,401,712 (describing non-woven fabrics utilizing fibers such as polyester, polypropylene, rayon, acrylics, blends of these synthetics or blends of these synthetics with natural fibers, and forming a web of such fibers by a conventional manner, including either by the wetlaid process, or by the drylaid process, and bonding the textile fibers together with a binding agent such as acrylic latexes, nitrile latexes, vinylchloride latexes, polyvinyl acetate, vinyl acetate-ethylenes, and styrene-butadine latexes); U.S. Pat. No. 6,673,358 (describing cellulosic fibrous webs, especially paper, air-laid and carded non-woven webs, spun-bonded and spun-lace webs, alveolar polymeric films, foam and other porous sheets); U.S. Pat. No. 6,613,729 (describing woven or nonwoven fibrous sheet materials, comprising synthetic or natural fibers or combinations thereof. Particular examples of nonwoven fibrous sheet materials, include meltblown, coform, air-laid, bonded-carded web materials, hydroentangled materials, or combinations thereof. Further examples include a coform basesheet of polymeric microfibers and cellulosic fibers, which typically comprise a gas-formed matrix of thermoplastic polymeric meltblown microfibers (such as, polypropylene microfibers) and cellulosic fibers (such as, for example, wood pulp fibers). An alternate description involves multiple layers of materials, such as a three layer composite which includes an elastomeric film or meltblown layer between two coform layers, wherein the elastomeric layer may include a material such as a metallocene polyethylene); U.S. Pat. No. 6,361,784 (describing, for example, spunbond webs comprising continuous fibers thermally bonded to one another, meltblown fibers comprising discontinuous fibers that are melt-bonded to adjacent fibers, and nonwoven web comprising very short fibers on the order of three millimeters or less); and U.S. Pat. No. 5,935,880 (describing, for example, water-dispersible fibrous nonwoven composite structures formed by a process comprising forming a wet-laid web from an aqueous suspension of pulp, hydraulically needling the web, adding a binder to one side of the web, creping the needled web, adding a binder to the second side, recreping the web, followed by drying and/or curing the web)).

Particular embodiments include an absorbent support that has at least one three-dimensionally textured surface. Such characteristic may be inherent to or formed with a particular type of fiber, or to a particular combination of fibers within a fiber matrix. A three-dimensionally textured surface may be produced in any manner known in the art, including for example, creping. As is known in the art, creping is "crinkling" of paper that occurs when the paper is dry (also called, dry creping) or during the paper-drying process. When the ridges and grooves imparted by the creping process are observable predominantly on the microscopic level, the creped surface is said to be "microcreped."

One particularly suitable microcreped absorbent support and its method of manufacture are described in PCT Pub. No. WO 02/076723. Micrex Corporation (Walpole, MA) provides the machinery capable of making the exemplar microcreped surface. Briefly, this exemplar microcreped absorbent support involves a non-woven self-supporting web of hydroentangled fibers, which include synthetic thermoplastic strength-providing fibers and absorbent or adsorbent fibers. This one example of an absorbent support is in a permanent, dry-creped, heat-set condition defining a succession of ridges and/or grooves in the overall body of the web. The thermoplastic fibers in the web may be heat set at the same time that the ridges and grooves are imparted to the web; thus, preserving the ridge and groove configuration during prolonged presence of a wetting agent in the absorbent support. Commercial suppliers or manufacturers of microcreped absorbent supports include, for example, DuPont (Wilmington, Del.) (see, for example, product name Sontara™), First Quality Nonwovens (Great Neck, N.Y.), and Kimberley Clark (Roswell, Ga.).

2. Wetting Agent

The disclosed wipes also include a cationic surfactant and a weak acid.

Representative cationic surfactants include, for example, isostearamidopropyl morpholine lactate (ISML), lapryium chloride, cetyltrimethylammonium bromide, di-dodecyldimethylammonium bromide, trimethylbenzylammonium chloride, diethyl ester dimethyl ammonium chloride, hexadecyltrimethylammonium, tetradecyl trimethyl ammonium bromide, cetylpyridinium chloride, alkyl $C_{12}$-$C_{14}$-dimethylbenzyl ammonium chloride, dodecyl pyridinium chloride, 11-(acryloyloxy)-undecyl-(trimethyl)-ammonium bromide, dimethyl dioctadecyl ammonium bromide, N-alkyl dimethylbenzyl ammonium chloride, or combinations thereof. In one embodiment, the cationic surfactant is ISML.

Representative weak acids include, for example, citric acid, acetic acid, ascorbic acid, glycolic acid, maleic acid, fumaric acid, benzoic acid, salicylic acid, nicotinic acid, cinnamic acid, tartaric acid, mandelic acid, or combinations thereof. Some exemplar wipes include citric acid as the weak acid.

The cationic surfactant and weak acid components of the disclosed wipes may be combined with the absorbent support in any manner known in the art. For example, a cationic surfactant and a weak acid may be applied to the absorbent support in liquid form, which liquid is absorbed into the support. The cationic surfactant and weak acid may be applied to the absorbent support in separate solutions or as a combined solution.

The solution(s) applied to the absorbent support may also include a variety of other components that may assist in providing the desired wiping and cleaning properties. For example, additional components may include water, other surfactants, emollients, preservatives, chelating agents, pH buffers, fragrances, or combinations thereof. In one example, the solution includes an amount of preservative effective to inhibit the growth of microorganisms in the wipe. Suitable preservatives are well known to those skilled in the art and may include, for example, parabens, sodiumhydroxymethylglycinate, DMDM hydantoin, benzalkonium chloride, and the like, or combinations thereof.

The total amount of solution applied to each absorbent support may vary depending upon the type of material being used for the absorbent support, the type of solution being used, the type of container being used to store the wipes, if any, and/or the desired end use of the wipes. In one embodiment, sufficient solution is added to adequately wet the absorbent support and yet avoid oversaturation of the absorbent support. Generally, each absorbent support can contain from about 150 to about 600 weight percent (such as, from about 250 to about 450 weight percent) based on the dry weight of the absorbent support. In a particular aspect, wherein the wipes include a microcreped absorbent support, such as is available from DuPont (Wilmington, Del.) (see, for example, product name Sontara™), First Quality Nonwovens (Great Neck, N.Y.), or Kimberley Clark (Roswell, Ga.), the amount of solution contained within the absorbent support is from about 5 ml/gm of support weight (500% weight percent) to about 10 ml/gm (1000% weight percent) based on the dry weight of the absorbent support.

Any concentration of cationic surfactant and weak acid may be present in or on an absorbent support following wetting of the absorbent support. Useful concentrations of cationic surfactant and weak acid on or in the absorbent support will depend, for example, upon the intended use of the disclosed wipe, and may be determined empirically by those of skill in the art. In particular embodiments, the concentration of cationic surfactant, such as ISML, in or on an absorbent support may be applied so that from about 50% to about 300% (w/w) surfactant is contained in the support material, including, for instance, from about 60% to about 275%, from about 70% to about 260%, or from about 75% to about 250% (w/w) surfactant contained in the support material. In other embodiments, the concentration of weak acid, such as citric acid, in or on an absorbent support may be applied so that from about 0.1% to about 10% (w/w) weak acid is contained in the support material, including, for instance, from about 0.5% to about 5%, from about 0.75% to about 4%, from about 1% to about 3.5%, or from about 1.3% to about 3% (w/w) weak acid is contained in the support material.

In some embodiments of the disclosed wipes, an ISML solution is applied to an absorbent support (for example, a 0.25 M ISML solution, e.g., 125 gm ISML per liter), so that from about 0.34 gm to about 2 gm ISML is applied to each gram of support material (for example, from about 0.6 gm to about 1.3 gm ISML per gram support material) depending on the liquid holding capacity of the support material. In particular embodiments, about 0.6 gm or about 2 gm ISML is applied per each gram of support material.

In other embodiments, a citric acid solution is applied to an absorbent support (for example, a 0.052 M (or 1%) solution, e.g., 1 gm/L citric acid), so that from about 0.01 gm to about 0.1 gm citric acid is applied per gram of support material (for example, from about 0.035 gm to about 0.07 gm citric acid per gram support material) depending on the liquid holding capacity of the support material. In particular embodiments, about 0.035 gm or about 0.1 gm citric acid is applied per each gram of support material.

No particular ratio need exist between the concentrations of a cationic surfactant and a weak acid in or on an absorbent support. In some examples, however, a weight ratio between the total amount of cationic surfactant and the total amount of weak acid can be about 12.5 parts cationic surfactant (such as, ISML) and about 0.5 parts weak acid (such as, citric acid).

In some embodiments, the wetted absorbent support will contain sufficient amounts or concentrations of cationic surfactant and/or weak acid to solubilize a metal. In particular examples, the amounts or concentrations of cationic surfactant and/or weak acid in or on an absorbent support will be sufficient to solubilize at least one of lead, cadmium, tin, barium, arsenic, chromium, copper, lead, mercury, silver, zinc, strontium, thallium, cobalt, germanium, zirconium, ionic forms of any thereof (such as, +2 cations), compounds containing any thereof (such as, oxides or halides thereof), or combinations thereof.

In more particular examples, a metal is solubilized when at least about 50%, at least about 60%, at least about 75%, at least about 80%, at least about 90%, at least about 95%, at least about 98%, or even 100% of the metal on the treated surface is dissolved by a cationic surfactant, weak acid or a combination of both present in the absorbent support, and/or by the combination of cationic surfactant, weak acid and mechanical displacement resulting from wiping the treated surface with a wipe. In other instances, a metal is solubilized when the amount or concentration of metal remaining on the surface is less than a PEL for the metal of interest; for example, at least about 5%, at least about 10%, at least about 15%, at least about 25%, at least about 50%, at least about 75%, at least about 80%, or at least about 90% less than a PEL.

In some embodiments, any solution containing ISML and citric acid as described above as a wetting agent can serve as a metal-removal composition in the absence of a wipe.

III. Methods for Removing Metals

Methods for removing metals from a surface are also disclosed herein. Such methods include applying a cationic surfactant and a weak acid to a surface, and wiping the surface with a three-dimensionally textured absorbent support.

Cationic surfactants, weak acids and useful concentrations of each, which are suitable for the disclosed methods, have been described above in Section II. Specific method embodiments involve ISML as a cationic surfactant and/or citric acid as a weak acid. In particular embodiments, the cationic surfactant and weak acid are in liquid form or are dissolved in a suitable solvent, such as, water. The cationic surfactant and weak acid may be mixed together to form a combined solution, or may be in the form of separate solutions.

In certain embodiments, the pH of a combined solution of cationic surfactant and weak acid (such as ISML and citric acid) or a separate solution of weak acid (such as citric acid) is less than about pH 5.0, less than about pH 4.5, less than about pH 4.0, or less than about pH 3.5. The pH of a combined solution of cationic surfactant and weak acid (such as ISML and citric acid) or a separate solution of weak acid (such as citric acid) in some examples of the disclosed methods may be in the range of about pH 3.0 to about pH 5.0, or about pH 3.0 to about pH 4.0.

In some embodiments, the cationic surfactant(s) and weak acid(s) can be applied one or more times directly to a surface; then (as described below in more detail), the surface is wiped with a three-dimensionally textured support. In some examples, the amount of cationic surfactant(s) and weak acid(s) applied to a surface (in separate solutions or a combined solution) is from about 0.0001 ml/cm$^2$ to about 0.05 ml/cm$^2$; for instance from about 0.0005 ml/cm$^2$ to about 0.025 ml/cm$^2$, from about 0.001 ml/cm$^2$ to about 0.01 ml/cm$^2$, or from about 0.002 ml/cm$^2$ to about 0.005 ml/cm$^2$. In a particular example, about 0.0036 ml/cm$^2$ of a combined solution including cationic surfactant (such as, ISML) and weak acid (such as citric acid) is applied to a surface (such as, human hands).

For a given volume per unit surface area, an ordinarily skilled artisan can readily calculate the weight of a particular solution component per unit surface area (such as mg/cm$^2$ cationic surfactant (e.g., ISML), or mg/cm$^2$ weak acid (e.g., citric acid)). For example, the volume per unit surface area ranges provide in the immediately preceding paragraph correspond to the following weights per unit surface for the indicated solutions:

| | Weight/Unit Area | |
|---|---|---|
| Volume/Unit Area | 1% solution (1 mg/ml) | 25% solution (25 mg/ml) |
| 0.0001-0.05 ml/cm$^2$ | 0.0001-0.05 mg/cm$^2$ | 0.0025-1.25 mg/cm$^2$ |
| 0.0005-0.025 ml/cm$^2$ | 0.0005-0.025 mg/cm$^2$ | 0.0125-0.625 mg/cm$^2$ |
| 0.001-0.01 ml/cm$^2$ | 0.001-0.01 mg/cm$^2$ | 0.025-0.25 mg/cm$^2$ |
| 0.002-0.005 ml/cm$^2$ | 0.002-0.005 mg/cm$^2$ | 0.05-0.125 mg/cm$^2$ |

In other method embodiments, a surface from which a metal is to be removed is wiped with a disclosed three dimensionally textured absorbent support containing a cationic surfactant and weak acid. Three-dimensionally textured absorbent supports (including those absorbent supports containing cationic surfactant and weak acid) useful in the disclosed methods have been described above (see Section II).

A wiping step of a disclosed method may be as brief or prolonged as is needed to remove a metal from a treated surface. For example, the duration of a wiping step may be no more than a few seconds (such as, no more than about 10 seconds, no more than about 15 seconds, or no more than about 30 seconds) or may be a minute or more. A single wiping movement or multiple wiping movements of an absorbent support across a surface may be employed.

Any surface actually or possibly contaminated with a metal may be treated using a disclosed method. Such surfaces include, for example, dermal surfaces, personal protective equipment (such as, safety glasses), clothing, shoes, workbenches, floors, walls, windowsills, equipment surfaces, furniture surfaces (such as tables, chairs), tools, or vehicular surfaces (such as, door handles, steering wheel, gear shift knob, visors, mirrors, or cigarette lighter).

It is contemplated that the disclosed methods may be useful to remove any metal(s) that may be solubilized in the presence of a cationic surfactant and weak acid. In some method embodiments, lead, cadmium, tin, barium, arsenic, chromium, copper, lead, mercury, silver, zinc, strontium, thallium, cobalt, germanium, zirconium, ionic forms of any thereof (such as, +2 cations), compounds containing any thereof (such as, oxides or halides thereof), or combinations thereof may be removed. Lead, lead ions, or lead-containing compounds (such as lead oxides or lead halides) or combinations thereof are removed in some particular embodiments.

Removing a metal from a surface involves displacing an amount or concentration of metal from a surface (such as, a dermal surface) by physical or chemical methods or a combination thereof. A substantial amount of metal is removed when, for example, the amount or concentration of metal remaining on the surface is less than a permissible exposure limit (PEL) for the metal of interest. In some instances the amount or concentration of metal remaining on the surface is at least about 5%, at least about 10%, at least about 15%, at least about 25%, at least about 50%, at least about 75%, at least about 80%, or at least about 90% less than a PEL.

PELs for various metals are known in the art. For example, in the United States, PELs for various metals are set by administrative rules promulgated by U.S. Government agencies. PELs for workplace exposure to various metals are established by Occupational Safety and Health Administration and are published at 29 C.F.R. Part 1910 (see, for instance, Tables Z-1, Z-2, and Z-3 in 37 C.F.R. §1910.1000, or 37 C.F.R. §1910.1025 (for lead), or 37 C.F.R. §1910.1027 (for cadmium)). Non-limiting exemplar PELs for various metals are shown in the following table:

| Metal | PEL (μg/day) |
|---|---|
| Lead | 500 |
| Cadmium | 25 |
| Arsenic | 50 |
| Chromium | 5000 |
| Nickel | 5000 |

Another non-limiting way to quantify the amount of metal removed from a surface is by the percentage of the initial metal load removed. In some specific examples, a substantial amount of metal is removed when at least about 25%, at least about 50%, at least about 75%, at least about 80%, at least about 90%, at least about 98% or even 100% of the metal originally present on the surface is displaced.

In some methods, a surface is first tested to determine whether a metal is present. Any method known in the art that is useful for detecting the presence of metal upon a surface may be employed in the disclosed methods. For instance, several chemical spot tests usually employing salts of rhodizonic acid (such as the sodium salt, the potassium salt, and the di-sodium salt) for the detection of lead in air, water, soil, dust, paint, and similar samples are known (see, for example, U.S. Pat. Nos. 5,010,020; 5,039,618; 5,330,917; 5,364,792; 5,416,028; 5,445,965; 5,496,736; 5,550,061; and 5,567,619).

Lead detection methods useful for testing skin contamination include, for example, U.S. Pat. No. 6,248,593. Briefly, U.S. Pat. No. 6,248,593 describes a method of detecting lead contamination on a surface using a handwipe to collect a sample of lead contamination from a surface. The lead is solubilized in the handwipe with an aqueous acid solution and treated with rhodizonate or sulfide anions. A change in color from pink to red, where rhodizonate anions are used, or brown to black, where sulfide anions are used, is indicative of the presence of lead. In particular embodiments of the U.S. Pat. No. 6,248,593 method, the lead is solubilized directly on the handwipe and the solubilized lead is treated with the color-forming anion directly on the handwipe (which has the advantage of preventing discoloration of the tested surface and further prevents contact between the skin and the colorimetric reagent). A kit for lead detection based on the method described in U.S. Pat. No. 6,248,593 is commercially available by the name Full Disclosure wipes from SKC, Inc. (Eighty Four, Pa.).

Another example of a metal detection method includes the test swabs described in U.S. Pat. No. 5,550,061 (see, also Lead Check™ test swabs, which are commercially available from Hybrivet Systems and its suppliers). Briefly, the test involves two glass ampules that contain an acid and a reagent. When the ampules are crushed, the chemicals mix together on a swab, which, when in contact with the metal of concern specifically reacts with the metal (such as, lead, chromium, nickel, cadmium, arsenic, mercury, or nickel). The impregnated swab is rubbed over the surface to be tested. The presence of a particular metal is determined by a reagent reaction on a swab containing a reagent specific for the metal.

The Macherey-Nagel Company (Duren, Germany) manufactures a test paper (PLUMBTESMO™) for the detection of lead. The PLUMBTESMO™ strips comprise a heavy filter paper with a reagent impregnated therein. To test for lead in a solution, a strip is dipped into the solution, and observed for a color change that indicates the presence of lead.

In more specific methods, a surface may be tested or retested for residual metal after a wiping a surface with an absorbent support. Any of the metal detection methods discussed throughout this specification are contemplated for the retesting step. In those instances where a retesting step indicates the presence of residual metal, some methods contemplate repeating metal removal steps (such as, applying a cationic surfactant and a weak acid, and wiping the surface with a three-dimensionally textured absorbent support). Such removal steps may be repeated a second or third or fourth time in some methods embodiments.

IV. Kits for Metal Removal

Kits for use in the removal, or detection and removal, of one or more metals (such as lead) are described herein. The disclosed kits are generally portable and permit the convenient removal, or detection and removal, of metals from surfaces, such as dermal surfaces.

Kits may include a carrier means, such as a box, a bag, or plastic carton. In one embodiment the carrier contains one or more containers, for instance sealed packets, vials, tubes, and the like, that include at least one wipe as disclosed herein. In some embodiments, the carrier includes disposable gloves to protect the user and/or a refuse container, such as a sealable plastic bag or lidded can or bottle, for use in disposing used wipe(s).

Instructions can be provided to detail the use of components of the kit, such as written instructions, video presentations, or instructions in a format that can be opened on a computer (e.g. a diskette or CD-ROM disk). These instructions indicate, for example, how to detect a metal using detection means in the kit, how to remove a metal from a surface using a wipe; how to retest a surface after wiping; and/or how to dispose of a contaminated wipe.

It is contemplated that the kits disclosed herein are useful for the removal, or detection and removal, of metals, including lead, cadmium, tin, barium, arsenic, chromium, copper, lead, mercury, silver, zinc, strontium, thallium, cobalt, germanium, zirconium, ionic forms of any thereof (such as, +2 cations), compounds containing any thereof (such as, oxides or halides thereof), or combinations thereof. In particular embodiments, the kits are useful for removal of lead, lead ions or lead-containing compounds, or detection and removal of lead, lead ions or lead-containing compounds (such as, lead oxides or lead halides).

The number of wipes supplied in the kit can be any appropriate number, depending for instance on the market to which the product is directed. For instance, if the kit is adapted for use in the field, the number of wipes provided would likely be an amount sufficient to remove metal(s), such as lead, from several different surfaces or individuals, perhaps in several different locales. Single use kits are also contemplated.

Specific provided kits contain a means for detection of a metal together with at least one disclosed wipe for metal removal. Such detection means can include any metal detection means that is sufficiently mobile and compact to be included in a kit intended for portable use, for example, at a site where heavy metal contamination is known or suspected. Such detection means may include, for example, calorimetric indicators, which use a chemical reaction that produces color to qualitatively or quantitatively identify metal contaminants. In particular embodiments, calorimetric indicators include, for example, chemically impregnated swabs, or calorimetric paper.

In certain kit embodiments, which are particularly useful for lead detection and removal, lead detection means involve wiping the test surface (such as, skin, safety glasses, tables, workbenches, shoes, or work equipment) with a lead detection wipe, spraying a mildly acidic aqueous solution onto the wipe to solubilize the lead, and then spraying an aqueous rhodizonate test reagent onto the wipe. If solubilized lead is present, a pink to red color bloom will appear on the wipe. Such lead detection means are known in the art, and are commercially available; see, for example, Full Disclosure™ wipes (SKC, Inc., Eighty Four, Pa.; see, also, U.S. Pat. No. 6,248,593).

Other lead detection means include chemical spot tests (employing salts of rhodizonate or sulfide anions) for the detection of lead in air, water, soil, dust, paint, and similar samples (see, for example, U.S. Pat. Nos. 5,010,020; 5,039,618; 5,330,917; 5,364,792; 5,416,028; 5,445,965; 5,496,736; 5,550,061; and 5,567,619). Still other detection means include the test swabs described in U.S. Pat. No. 5,550,061 and PLUMBTESMO™ test strips (both of which are described in more detail above).

The following examples are provided to illustrate certain particular features and/or embodiments. These examples should not be construed to limit the invention to the particular features or embodiments described.

EXAMPLES

Example 1

Comparison of Methods for Removing Lead from Human Skin

This example demonstrates the efficacy of a system comprising citric acid and ISML on a textured wipe to remove lead from skin. In this example, several approaches for removing lead from the hands were evaluated using a hand decontamination protocol that entailed applying known quantities of a prepared mixture of lead and corn starch powder to the hands and then washing it off. Corn starch was used as a diluent to facilitate the weighing and handling of small quantities of lead. The corn starch/lead mixture, when applied to the hands, resulted in an initial lead load of 3000 μg or approximately 10 μg/cm$^2$ skin concentration on the palm of the hand. This initial lead load on the hands was similar to the upper range of loadings found in NIOSH field surveys (Esswein et al., NIOSH Health Hazard Evaluation Report No. 94-0268-2618, Standard Industries, San Antonio, Tex., CDC/NIOSH: Cincinnati, Ohio, 1996).

Red lead oxide (PbO)>99.9%, <10 μm, was mixed uniformly into food grade corn starch by rotary tumbling to produce a concentration of 90.9 mg/gram (9% w/w). Exactly 33 milligrams of the mixture was weighed out onto folded waxed weighing paper for later transfer to the palms.

The prepared lead mixture was applied to a single palm and, then, was carefully rubbed into the palms of both hands for 30 seconds so that the lead mixture was evenly distributed. This lead application step was immediately followed by applying the skin cleanser being evaluated, which was rubbed into the palmer skin and dorsal side of the hands for 30 seconds. Next, the hands were rinsed under running tepid tap water for 30 seconds and finally patted dry with a paper towel.

To measure the relative amount of lead remaining on the skin after the cleaning process, lead-detection hand wipes with Palintest™ media (Palintest USA, Erlanger, Ky.) or GhostWipes™ (Environmental Express, Mt. Pleasant, S.C.) were used. Comparative testing determined either media to have similar lead sampling efficiency. For each trial, three consecutive hand wipes were performed for 30 seconds each and put into a conical plastic storage container. For these samples, the lower limit of detection was calculated to be 0.6 μg Pb per sample and the limit of quantification was 2.0 μg Pb per sample.

FIG. 1 shows the amount (in μg Pb) of an initial 3000 μg lead load remaining on the skin following four methods of skin cleaning, including common soap and water alone ("S+W"), liquid mixtures of citric and ISML ("C-I") or acetic acid and ISML ("A-I") applied without a wiping towel, and a mixture of citric and ISML applied with a wiping towel ("C-I wipe"). The fabric material used for the C-I wipe was a commercial wipe product (Pampers Baby Wipes™, Procter & Gamble Co., Cincinnati, Ohio), which was pre-dried. When the wipe was dry, 5.5 ml of a solution consisting of 4.25% citric acid and 3.75% ISML in water was added to the pre-dried wipes. The individual trial evaluations consisted of five replicate runs using the standardized approach described above.

As shown in FIG. 1, common soap and water alone ("S+W") were not particularly effective in removing deposited lead from human skin. In comparison, a citric acid and ISML formulation on a fabric wipe ("C-I wipe") was most effective at removing lead from the skin. Mixtures of citric and ISML ("C-I") and acetic acid and ISML ("A-I") applied without a wiping towel were also effective at removing lead. The finding that a C-I wipe is somewhat more effective than C-I applied in solution to the skin indicates that the mechanical action of a wipe contributes to the lead removal process.

Example 2

C-I Wipes Provide Superior Lead Removal

In this Example, several variations on the use of a C-I wipe were tested for efficacy at removing lead from hands. In this set of comparisons, test participants knew the identity of the product being tested (i.e., this was a non-blind test).

As described in Example 1, 3000 μg of Pb in corn starch was applied and rubbed into the palms of the test participants' hands. Thereafter, one of five different protocols, each using Micrex™ heavily creped wiping towels, was performed. Except where otherwise noted, the hands were then rinsed under running tepid tap water for 30 seconds and patted dry with a paper towel. The cleansing protocols are summarized as follows:

| Protocol | Description |
|---|---|
| A | Wipe containing 10 mL of 0.5% citric acid and 12.5% ISML solution |
| B | Wipe containing 10 mL of 0.25% citric acid and 18.75% ISML solution |
| C | Protocol B but without a final water rinse |
| D | Protocol B but with a second use of the wipe prior to rinsing |
| E | Use of wipe wetted with water only, followed by a water rinse |
| T | Protocol B followed by a second citric acid and ISML wipe, but no water rinse |

Figure 2:
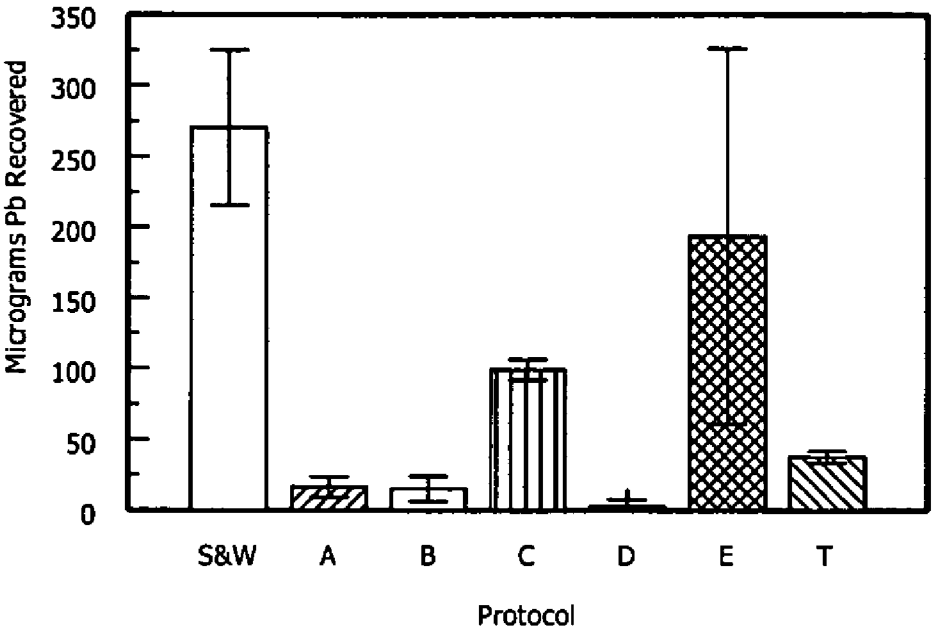
FIG. 2 is a bar graph showing the amount a 3000 μg initial lead load remaining on human hands following various cleansing protocols involving one or more C-I wipes as described in Example 2 (Protocols A, B, C, D and T), or a wipe wetted only with water (Protocol E).

For comparison, test participants also used a common industrial hand cleanser (Smart & Final™ Liquid Soap, Los Angeles, Calif.) in accordance with manufacturer directions ("S&W" in FIG. 2).

As shown in FIG. 2, Protocols A and B (using two different concentrations of citric acid and ISML) were equally effective at removing lead from human skin with 16.1 and 14.8 μg, respectively, of an initial 3000 μg lead load measured on the hands after cleansing in this manner. Using the method of Protocol C, 98.8 μg lead remained on the hands. The Protocol C result indicates that rinsing after using a C-I wipe may assist lead removal from the skin surface, possibly by dilution of the solubilized lead. As shown by the Protocol D result, using a C-I wipe twice with rinsing with water removes almost all lead, with only 2.5 μg lead remaining on the skin. When two consecutive C-I wipes were used without a final water rinse (i.e., Protocol T), lead was also effectively removed from skin (37.2 μg measured on skin after cleansing protocol). Protocol T could be used in a remote location where water for rinsing was not available.

In stark comparison to each of the protocols involving one or more C-I wipes, the use of a wetted wipe with no surfactant or citric acid (i.e., Protocol E) was less effective for lead removal (193.3 μg lead remaining) from skin. Similarly, use of common soap (Smart & Final™ Liquid Soap, Los Angeles, Calif.) and water as cleansing agents ("S&W") resulted in 270 μg of lead remaining on the hands, which demonstrates the relative ineffectiveness of this widely used method for lead removal.

Example 3

Additional Comparative Tests

This Example demonstrates that C-I wipes are superior lead-removal compositions when compared side-by-side with several other commercial products. In this Example, C-I wipes were prepared by adding 10 mL of solution containing 0.5% citric acid and 12.5% ISML in water to Micrex™ wipe towels. The protocol described in Example 1 was used to contaminate and cleanse the hands.

Some of the commercial products tested claim in advertisements to be effective in removing lead from skin, including D-Lead™ without scrubbers ("Cleanser U"), D-Lead™ with scrubbers ("Cleanser N") (Esca Tech, Milwaukee, Wis.), and Clean-All™ ("Cleanser F") (Sasha International, Miami Beach, Fla.). Other commercial products that are sold for industrial skin cleansing were also included in the side-by-side testing described below, including Kresto Select™ with scrubber ("Cleanser H") (Stockhausen, Greenboro, N.C.), Kresto Kwik™ Wipes ("Cleanser G") (Stockhausen, Greenboro, N.C.), and GoJo Multigreen™ with scrubbers ("Cleanser I") (GoJo Corp., Akron, Ohio). The scrubbers in these products may consist of ground walnut shell, plastic, or crystalline sand and may irritate the skin with repeated use. These comparison products were selected as among the most widely used and most available heavy duty scrubbers on the commercial market.

Figure 3:
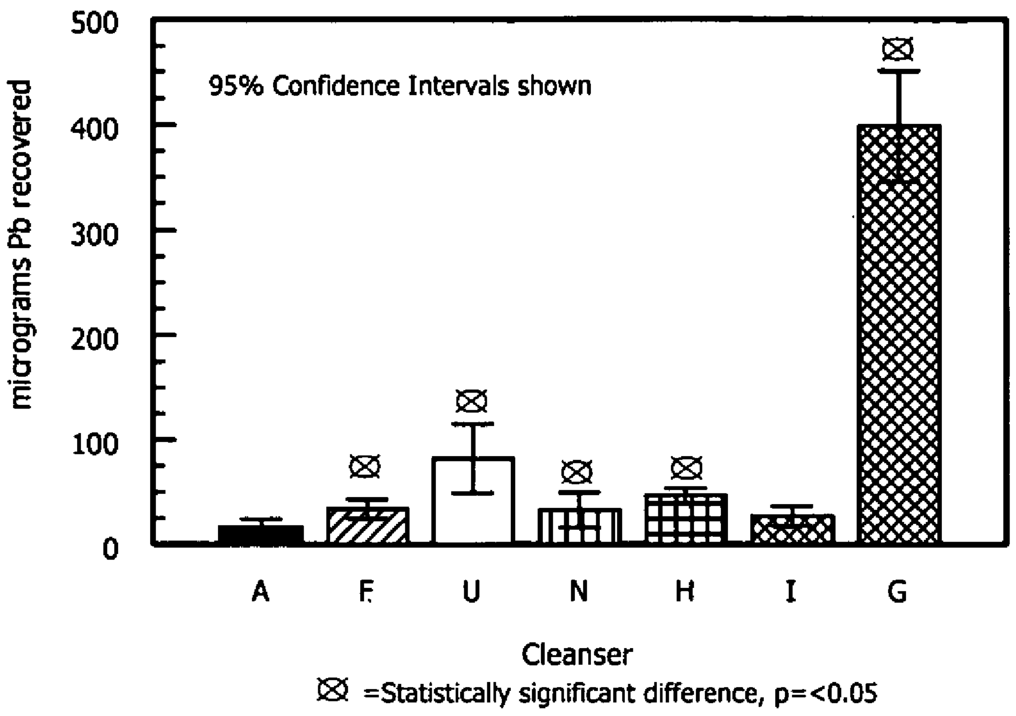
FIG. 3 is a bar graph showing the amount a 3000 μg initial lead load remaining on the hands after cleaning with a C-I wipe (Cleanser A), various commercially available industrial hand cleansers (Cleansers F, U, N, H, I and G), as further described in Example 3.

FIG. 3 shows the comparison lead measured on human skin following cleansing with a C-I wipe ("Cleanser A) and each of Cleansers F, U, N, H, I, and G. The C-I wipe ("Cleanser A") provided statistically significant superior lead cleansing from human hands when compared to Cleansers F, U, N, H, and G. The C-I wipe removed more lead from skin than did Cleanser I (16.1 and 26.5 μg Pb, respectively, remaining on hands following cleaning); however, the difference was not statistically significant given the number of test replicates. A significant difference is expected with comparisons using a larger test population.

Example 4

Blind Comparison Testing

In this Example, further comparisons between C-I wipes and other cleansing methods are described. In this case, comparisons were conducted using 14 participants, who were blinded to the identity of the test products. Each test subject was provided with a randomly selected cleanser and each product was used twice. After each use, the test subjects were asked to rank the cleanser's cleaning power, its odor, and its feel on the skin on a scale of 1 (poor) to 5 (good). The cleansers compared were (i) a C-I wipe (10 mL of 0.5% citric acid and 12.5% ISML on a 8×8" (20 cm×20 cm) Micrex™ wipe) ("Cleanser A"); (ii) D-Lead™ liquid soap without scrubbers ("Cleanser B"); (iii) Clean-All™ Liquid Soap (Sasha International, Miami Beach, Fla.) ("Cleanser C"); and (iv) Ivory™ Liquid Soap (Procter and Gamble Co., Cincinnati, Ohio) ("Cleanser D"). Two (2) mL of each of the liquid soaps (i.e., Cleansers B, C, and D) were applied to the palms.

Figure 4:
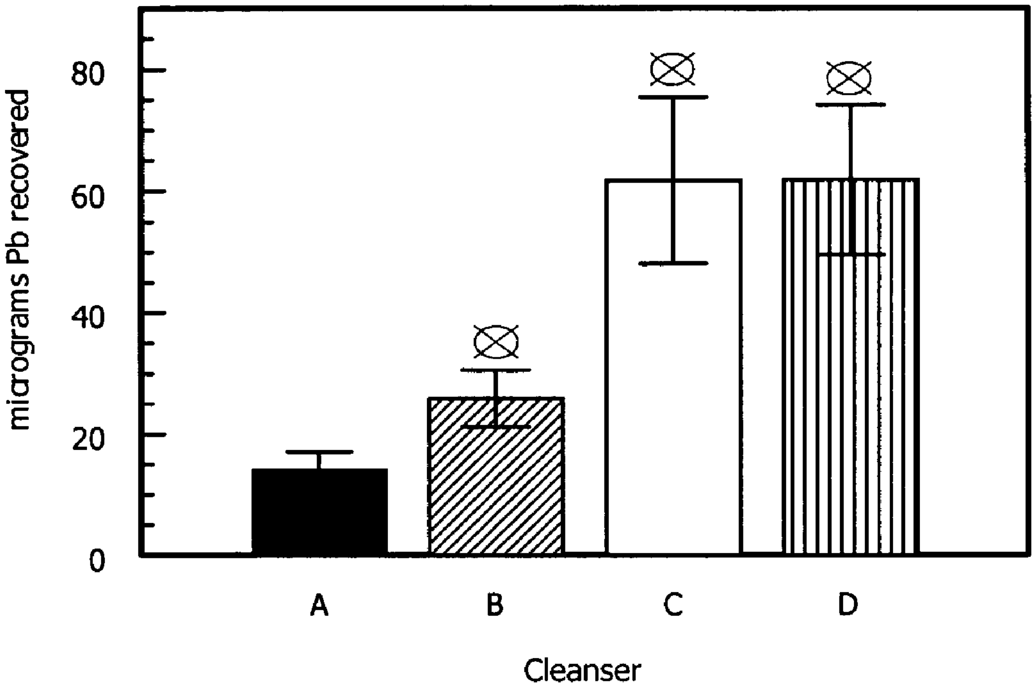
FIG. 4 is a bar graph showing the amount of a 3000 μg initial lead load remaining on the hands of blinded study participants after using a C-I wipe ("Cleanser A"), D-Lead™ liquid soap without scrubbers ("Cleanser B"), Clean-All™ Liquid Soap ("Cleanser C"), or Ivory™ Liquid Soap ("Cleanser D").

FIG. 4 shows the results of comparisons of Cleansers A-D. In these blinded-use comparisons, the C-I wipe system removed more lead from the hands than each of the other products. These results were statistically significant. Cleanser C, which is advertised to remove lead, removed no more lead than the non-industrial Ivory™ Liquid Soap (i.e., Cleanser D).

The results of the user opinion survey performed during the use of each of the above cleansers during the blinded tests are shown below:

| Cleanser | Cleansing Power | Odor | Feel |
|---|---|---|---|
| A | 3.50 | NA | 3.54 |
| B | 3.68 | 3.77 | 3.75 |
| C | 3.4 | 3.29 | 3.48 |
| D | 3.64 | 3.71 | 3.71 |

The results in the foregoing table demonstrate that participants who used each of these cleansers did not view them (on average) as being noticeably different in their perceived ability to clean the skin or how they felt when used. The C-I wipe as used in this Example is not odoriferous in its present embodiment; although a fragrance could be added to the formulation.

Example 5

Non-Toxicity of ISML and Citric Acid

ISML is commercially available for formulation in personal hygiene products such as hair conditioners and shampoo, massage lotions, aerosol mousse and children's detangler for hair, where it is used in concentrations of between 1 and 5%. In 1999, the Cosmetic Ingredient Review (CIR) Expert Panel (established by the Cosmetic, Toiletry, and Fragrances Association to regularly examine the potential health effects of ingredients that might be used in cosmetics) concluded that ISML was considered safe for use in rinse-off cosmetic products. ISML is not listed as toxic by the U.S. Toxic Substance Act (TSCA) open inventory, nor is it listed on the European Inventory of New and Existing Chemical Substances (AICS).

Citric acid is widely used as a preservative in many topical cosmetic and medicinal products at a concentration of about 0.1%. Citric acid is an alpha-hydroxy acid and in one clinical treatment study, a 10% citric acid lotion was applied topically for a three month period (Bernstein et al., *Dermatol. Surg.,* 23:689-694, 1997). No clinical signs of adverse effects were noted.

Example 6

ISML in Combination with Citric Acid does not Promote Lead Penetration into Skin It is known that some commonly used anionic surfactants, such as sodium lauryl sulfate, can enhance the skin penetration of several tested organic compounds and also certain tested inorganic compounds, such as nickel (Cumberbatch et al., *Toxicology,* 77(12):181-191, 1993; Emilson et al., *Acta Dermato-Venereologica,* 73:203-207, 1993; Frankild et al., *Contact Dermatitis,* 32:338-345, 1995; Lindberg et al., *Scanning Microscopy,* 3:221-324, 1989; Nielsen, *Int. J. Occup. Environ. Health,* 6:143-147, 2000; Seidenari, *Acta Dermato-Venereologica,* 74:245-249, 1994; Wilhelm et al., *J. Invest. Dermatol.,* 96:963-967, 1991). Thus, the in vitro skin penetration enhancement effect of a cleanser comprising ISML and citric acid was determined. As shown in this Example, ISML in combination with citric acid does not promote lead penetration into skin.

Full thickness human abdominal skin was obtained from the Università degli Studi di Trieste, Unità di Medicina del Lavoro, Trieste (Italy) as surgical waste. The skin was excised, immediately placed in plastic bags, and stored in a freezer (−25° C.), for a period up to, but not exceeding, 4 months. The abdominal skin was mounted in a two-chamber testing device as described in Franz, *J. Invest. Dermatol.,* 93:633-640, 1975. Skin was mounted so that the exterior surface faced the donor chamber and the dermis faced the receptor chamber. On the donor side of the skin, lead oxide dust (<100 μm particles) was applied at a concentration loading of 5 mg/cm$^2$ skin, followed by the addition of 2 ml of synthetic sweat. Synthetic sweat was prepared as described by Liden and Carter (*Contact Dermatitis,* 44:160-165, 2001). Briefly, a solution of deionised and aerated water at room temperature (20° C.) containing 0.5% sodium chloride, 0.1% lactic acid and 0.1% urea was prepared and adjusted to pH 5.0 with ammonia. The artificial sweat solution was used within 3 hours of preparation.

Eight replicate tests were conducted for each set of conditions. In one set of tests, nothing more was done to the skin until 24 hours when the test was stopped. In a second set of tests, Ivory™ Liquid Soap, containing sodium lauryl sulfate and sodium laureth sulfate, was used with cotton balls to decontaminate the skin after 30 minutes; the skin was then remounted in the penetration cell for the remaining 24 hours with only synthetic sweat solution added to the donor side. In a third set of tests, a solution of 12.5% ISML and 0.5% citric acid was used with cotton balls to decontaminate the skin after 30 minutes; the skin was then remounted as in the second set of experiments. At 24 hours the skin was removed from all test cells, carefully cleaned with running water and the remaining content of lead determined in the skin. The receptor chamber fluid was also analyzed for lead. All samples were analyzed for lead using electro-thermal atomic absorption spectrometry with Zeeman background correction, according to NIOSH Method 7105 (*NIOSH Manual of Analytical Methods,* 4th Ed., ed. by Schlecht and O'Connor, Washington D.C.:U.S. Government Printing Office, August 1994, as supplemented by 1st Supplement Publication 96-135, 2nd Supplement Publication 98-119, and 3rd Supplement 2003-154). The above three sets of experiments were also repeated using skin that had been damaged by lightly drawing a hypodermic needle across the skin surface.

The results of these experiments demonstrate that the cleanser containing ISML and citric acid did not statistically increase the amount of lead penetration into the receptor fluid through intact skin when used as described. However, the Ivory™ Liquid cleanser did increase penetration by almost 8-fold (Mann-Whitney U-test, $p=0.0002$). The difference in penetration between the cleanser containing ISML and citric acid and Ivory Liquid cleanser was also significant when analyzed separately.

Penetration of lead through damaged skin was 5.6 times greater then through intact skin when no cleansers were used. When the cleansers were tested on damaged skin, penetration of lead in the ISML and citric acid cleanser group was 1.6-fold greater than for the no treatment group and was statistically significant ($p=0.01$). Skin penetration for the test cells in which Ivory Liquid soap had been used contained 4.4 times more lead than those skins that had not been treated with a cleanser ($p=0.0003$). The difference between the ISML and citric acid cleanser and Ivory Liquid soap was statistically significant ($p=0.005$).

The skin content of lead remaining in the skin after removing the skin from the test cells was similar in intact and damaged skin (392 versus 344 ng/cm$^2$). In the test cells in which the ISML and citric acid cleanser was used, there was a 27-fold reduction in the intact skin set and a 9-fold reduction in the damaged skin set in the amount of lead found present in the skin. When the Ivory Liquid cleanser was used, there was an 11-fold reduction and a 2-fold reduction, respectively. The difference in the amount of lead remaining in the skin between the ISML and citric acid cleanser and Ivory Cleanser in intact skin was not statistically significant but it was statistically significant for damaged skin.

When the sum of the skin content and penetrated lead was used to compare cleansers, the difference was highly significant. This demonstrates that the ISML and citric acid cleanser did not enhance penetration of lead into or through the skin when used, and was more effective at removing lead from the skin, whereas the other common cleanser increased penetration and skin content of lead.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A dermal surface wipe, comprising:

a three-dimensionally textured absorbent support, wherein the absorbent support is textured with protrusions visible to the naked eve, such protrusions capable of providing frictional resistance when the absorbent support is moved across a dermal surface;

isostearamidopropyl morpholine lactate (ISML) in the absorbent support; and citric acid in the absorbent support.

2. The wipe of claim 1, wherein the amount of ISML in the absorbent support is from about 0.3 gm to about 2 gm ISML per gram of absorbent support.

3. The wipe of claim 2, wherein the amount of citric acid in the absorbent support is 0.01 gm to about 0.1 gm citric acid per gram of absorbent support.

4. The wipe of claim 1, wherein the amount of ISML is from about 0.6 gm to about 1.3 gm ISML per gram of absorbent support, and the amount of citric acid is from about 0.03 gm to about 0.07 gm citric acid per gram of absorbent support.

5. The wipe of claim 1, wherein the weight ratio of the amount of ISML to the amount of citric acid in the absorbent support is 12.5 parts ISML to about 0.5 parts citric acid.

6. The wipe of claim 1, wherein the amounts of ISML and citric acid in the absorbent support are sufficient to solubilize at least 100 μg lead.

7. A wipe, consisting essentially of:

a three-dimensionally textured absorbent support, wherein the absorbent support has a rough surface with a succession of ridges and grooves above the surface of the absorbent support that are visible to the naked eve;

ISML; and a weak acid comprising citric acid, or acetic acid, or a combination thereof;

wherein the amounts of ISML and the weak acid(s) in the wipe are sufficient to solubilize a metal comprising lead, cadmium, tin, barium, arsenic, chromium, copper, mercury, silver, zinc, strontium, thallium, germanium, or zirconium, or a combination thereof.

8. The wipe of claim 7, wherein the metal is lead.

9. A method for removing metals from a surface, comprising:

applying a cationic surfactant and a weak acid to a surface; and wiping the surface with a three-dimensionally textured absorbent support, wherein the support is textured with protrusions that are visible to the naked eye;

wherein the protrusions frictionally engage the surface during wiping the surface to remove at least about 50% of at least one metal from the surface.

10. The method of claim 9, wherein the cationic surfactant is JSML, lapryium chloride, cetyltrimethylammonium bromide, di-dodecyldimethylammonium bromide, trimethylbenzylammonium chloride, diethyl ester dimethyl ammonium chloride, hexadecyltrimethylammonium, tetradecyl trimethyl ammonium bromide, cetylpyridinium chloride, alkyl $C_{12}$-$C_{14}$-dimethylbenzyl ammonium chloride, dodecyl pyridinium chloride, 11-(acryloyloxy)undecyl(trimethyl)

ammonium bromide, dimethyl dioctadecyl ammonium bromide, or N-alkyl dimethylbenzyl ammonium chloride, or a combination thereof.

11. The method of claim 10, wherein the cationic surfactant is ISML.

12. The method of claim 11, wherein the concentration of ISML on the surface is from about 25 $\mu g/cm^2$ to about 250 $\mu g/cm^2$.

13. The method of claim 11, wherein the weak acid is citric acid, acetic acid, ascorbic acid, glycolic acid, maleic acid, fumaric acid, benzoic acid, salicylic acid, nicotinic acid, cinnamic acid, tartaric acid, or mandelic acid, or a combination thereof.

14. The method of claim 13, wherein the weak acid is citric acid.

15. The method of claim 14, wherein the concentration of citric acid on the surface is from about 1 $\mu g/cm^2$ to about 10 $\mu g/cm^2$.

16. The method of claim 9, wherein the weak acid has a pH that is not harmful to skin.

17. The method of claim 9, wherein the metal is lead, cadmium, tin, barium, arsenic, chromium, copper, mercury, silver, zinc, strontium, thallium, germanium, or zirconium, or a combination thereof.

18. The method of claim 17, wherein the metal is lead.

19. The method of claim 9, wherein the cationic surfactant and the weak acid are contained on or within the absorbent support.

20. The method of claim 9, wherein the surface comprises a dermal surface.

21. The method of claim 9, wherein wiping the surface removes at least about 95% of at least one metal from the surface.

22. A method for removing lead from a dermal surface, the method comprising:

(a) providing an absorbent support comprising:
 a three-dimensionally textured surface, wherein the textured surface has protrusions visible to the naked eye,
 at least about 50% (w/w) of a cationic surfactant,
 at least about 0.5% (w/w) of a weak acid; and (b) wiping a dermal surface with the absorbent support for about 10 seconds to about 1 minute to remove lead from the dermal surface.

23. The method of claim 22, wherein the cationic surfactant comprises ISML, and the weak acid comprises citric acid, acetic acid or a combination thereof.

24. The method of claim 22 further comprising testing for the presence of lead on the dermal surface prior to steps (a) and (b).

25. A method for detecting and removing lead from a surface comprising:

(a) detecting lead on a surface by a method comprising:
 (i) wiping the surface with a first wipe whereby residue containing lead contamination, if present on the surface, is retained and collected on the first wipe;
 (ii) solubilizing any lead collected on the first wipe with an acidic aqueous solution having a pH of about 1 to about 5, wherein the acidic solution is not present on the first wipe during step (i) and, wherein the lead is solubilized on the first wipe;
 (iii) treating the solubilized lead with an anion selected from the group consisting of rhodizonate or sulfide; and
 (iv) observing a color formed in step (iii); wherein, if lead is present on the surface, the color formed is pink to red if the anion is rhodizonate or the color is brown to black if the anion is sulfide; and (b) removing lead by wiping the surface with a second wipe comprising:
 (i) a three-dimensionally textured absorbent support,
 (ii) isostearamidopropyl morpholine lactate (ISML) in the absorbent support, and
 (iii) citric acid in the absorbent support.

26. A method for removing metal from a dermal surface, comprising:

applying to a dermal surface contaminated by a metal amounts of ISML and citric acid sufficient to solubilize the metal; and removing the ISML, the citric acid, and the metal from the dermal surface by wiping the dermal surface with a three-dimensionally textured absorbent support. the support textured with protrusions visible to the naked eye, wherein the metal remaining on the dermal surface after wiping is an amount at least about 5% below a permissible exposure limit for the metal.

27. The method of claim 26, wherein the metal is lead.

* * * * *

UNITED STATES PATENT AND TRADEMARK OFFICE

CERTIFICATE OF CORRECTION

PATENT NO. : 7,604,997 B2
APPLICATION NO. : 11/039178
DATED : October 20, 2009
INVENTOR(S) : Esswein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

Signed and Sealed this

Fifth Day of October, 2010

David J. Kappos

*Director of the United States Patent and Trademark Office*

UNITED STATES PATENT AND TRADEMARK OFFICE

CERTIFICATE OF CORRECTION

PATENT NO. : 7,604,997 B2
APPLICATION NO. : 11/039178
DATED : October 20, 2009
INVENTOR(S) : Esswein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1307 days.

On the Cover, in Other Publications:

"Burr et al., Niosh" should read --Burr et al., NIOSH--

In two instances, "Esswein et al., Niosh" should read --Esswein et al., NIOSH--

In the Specification:

Column 1, line 50, "port" should read --Port--

Column 2, line 13, "Komecki" should read --Kornecki--

Column 3, line 10, "lead" should be deleted (duplicate)

Column 3, line 18, "lead" should be deleted (duplicate)

Column 4, line 13, "amount a 3000" should read --amount of a 3000--

Column 4, line 18, "amount a 3000" should read --amount of a 3000--

Column 4, line 57, "agent)" should read --agent")--

Column 5, line 29, "effect" should read --affect--

Column 5, line 43, "lead" should be deleted (duplicate)

Column 5, line 46, "$Pd^{2+}$ $Pt^{2+}$ $Hg^{2+}Zn^{2+}$" should read --$Pd^{2+}$, $Pt^{2+}$, $Hg^{2+}$, $Zn^{2+}$--

Signed and Sealed this

Second Day of November, 2010

David J. Kappos
*Director of the United States Patent and Trademark Office*

Column 6, line 25, “damage to” should read --damage--

Column 7, line 19, “wet wipe” should read --wet wipes--

Column 7, line 23, “Industy” should read --Industry--

Column 7, line 29, “others.” should read --others.)--

Column 7, line 40, “and or” should read --and/or--

Column 8, line 28, “characteristic” should read --characteristics--

Column 10, line 35, “lead” should be deleted (duplicate)

Column 11, line 35, “provide” should read --provided--

Column 12, line 9, “lead” should be deleted (duplicate)

Column 13, line 25, “nickel” should be deleted (duplicate)

Column 13, line 35, “a wiping a” should read --wiping a--

Column 13, line 44, “methods” should read --method--

Column 14, line 4, “lead” should be deleted (duplicate)

Column 14, line 25, “calorimetric” should read --colorimetric--

Column 14, line 28, “calorimetric” should read --colorimetric--

Column 14, line 29, “calorimetric” should read --colorimetric--

Column 17, line 18, “(“Cleanser A)” should read --(“Cleanser A”)--

Column 18, line 44, “3:221-324” should read --3:221-224--

Column 19, line 39, “then” should read --than--

Column 20, line 13, “eve” should read --eye--

Column 20, line 39, “eve” should read --eye--

Column 20, line 61, “JSML” should read --ISML--

Column 21, line 8, “$\mu g/cm^{2.}$” should read --$\mu g/cm^2$.--

Column 22, line 38, “support. the” should read --support, the--